United States Patent
Huang et al.

(10) Patent No.: US 11,369,627 B2
(45) Date of Patent: Jun. 28, 2022

(54) MYRTLE POLYSACCHARIDE P1, THE SEPARATION METHOD THEREOF AND THE USE IN PREPARING HYPOLIPIDEMIC DRUGS THEREFOR

(71) Applicant: South China Normal University, Guangzhou (CN)

(72) Inventors: Ruqiang Huang, Guangzhou (CN); Jinghui Wang, Guangzhou (CN); Qian Wang, Guangzhou (CN); Linlin Gao, Guangzhou (CN); Jingwen Zhang, Guangzhou (CN)

(73) Assignee: South China Normal University School of Life Sciences, Guangzhou (CN)

( * ) Notice: Subject to any disclaimer, the term of this patent is extended or adjusted under 35 U.S.C. 154(b) by 0 days.

(21) Appl. No.: 16/435,677

(22) Filed: Jun. 10, 2019

(65) Prior Publication Data
US 2020/0069724 A1   Mar. 5, 2020

(30) Foreign Application Priority Data
Aug. 28, 2018 (CN) .......................... 201810986675.6

(51) Int. Cl.
*A61K 31/715* (2006.01)
*A61P 3/06* (2006.01)
*C08B 37/00* (2006.01)

(52) U.S. Cl.
CPC .............. *A61K 31/715* (2013.01); *A61P 3/06* (2018.01); *C08B 37/0003* (2013.01); *C08B 37/006* (2013.01)

(58) Field of Classification Search
CPC .............. A61K 31/715; C08B 37/0003; C08B 37/006; A61P 3/06
USPC .......................................................... 514/54
See application file for complete search history.

(56) References Cited

FOREIGN PATENT DOCUMENTS

CN    101319185 A    12/2008
CN    104262500 A    1/2015

OTHER PUBLICATIONS

Chidouh et al. (Food Hydrocolloids 35 (2014) 733-739).*
Chen et al. (Biomed. Chromatogr. 13: 11-14 (1999).*
Qin et al. (Food Sci Nutr. 2018;6:1621-1628).*
Galvão et al. (Rev Bras Farmacogn 24(2014): 683-690).*
Haciseferoğullan et al. (J Food Sci Technol (Jan.-Feb. 2012) 49(1):82-88).*
Khan et al. (Afr. J. Pharm. Pharmacol. vol. 8(8), pp. 235-239, Feb. 28, 2014).*
Gao et al. (J. Agric. Food Chem. 2017, 65, 9790-9798).*
Barbana et al. (Food Research International 44 (2011) 174-180).*
Story et al. (J. Nutr. 106: 1292-1294, 1976).*
Chinese Office Action dated Apr. 27, 2020, Application No. CN201810986675.6.

* cited by examiner

*Primary Examiner* — Shaojia A Jiang
*Assistant Examiner* — Michael C Henry
(74) *Attorney, Agent, or Firm* — The Dobrusin Law Firm, PC

(57) ABSTRACT

The invention discloses a myrtle polysaccharide P1, the separation method thereof and the use in preparing hypolipidemic drugs therefor, wherein the P1 contains 6.74% of ribose, 1.73% of rhamnose, 60.06% of arabinose, 3.54% of xylose, 5.64% of mannose, 13.16% of glucose, and 9.13% of galactose. The experiment result shows that the myrtle polysaccharide P1 has a certain ability to bind cholate in vitro. Taking cholestyramine as a positive control and the binding rate of cholestyramine to each cholate as 100%, the relative binding rate of the myrtle polysaccharide P1 to sodium taurocholate, sodium glycocholate and sodium cholate was 25.28%, 44.56%, and 50.10%, respectively.

4 Claims, 3 Drawing Sheets

MYRTLE POLYSACCHARIDE P1, THE SEPARATION METHOD THEREOF AND THE USE IN PREPARING HYPOLIPIDEMIC DRUGS THEREFOR

TECHNICAL FIELD

The invention belongs to the field of natural product (drug), and specifically, relates to a myrtle polysaccharide P1, the separation method thereof and the use in preparing hypolipidemic drugs therefor.

BACKGROUND

Myrtle (*Rhodomyrtus tomentosa*) is also named Gangren (Guangdong), Dourengan (Guangxi), Shidurenzi ("Bencaoshiyi"), Daorenzi ("Lingbiaoluyi"), or Daonianzi ("Sushenliangfang"), etc., and is widely distributed in southern subtropical region; it is a dominant species with a coverage of 30-60% and is a pioneer community in the evergreen broad-leaved forest ecosystem; in China, it is mainly distributed in Lingnan area and is the main understory vegetation in southern China with abundant resources. Most of them are born in hilly slopes, wilderness and roadsides, and the wild myrtle is widely distributed. However, its percentage of utilization and level of processing are low, showing that myrtle is a potential new food resource for large scale development and utilization.

The fruit of myrtle is a berry. When ripe, the skin becomes purple-black, and the flesh becomes purple-red. The meat thereof is juicy and nutritious. Studies have shown that in a mature wild myrtle fruit, the content of total sugar accounts for 8.06%, reducing sugar accounts for 7.72%, pectin accounts for 1.01%, total acid accounts for 0.38%, protein accounts for 1.30%, fat accounts for 0.32%, starch accounts for 3.08%, and crude fiber accounts for 34.97%; the content of vitamin C is 5.48 mg/kg.

Myrtle fruit contains polysaccharides, flavonoids, saponins, polyphenols, terpenoids and other active ingredients, and has biological activities such as anti-oxidation, anti-aging, anti-inflammatory, antibacterial and liver protection. As a wild plant resource, myrtle has bright prospects in food processing, health product development and medical drug research.

SUMMARY OF THE INVENTION

A primary object of the present invention is to provide a myrtle polysaccharide P1 which is highly pure and biologically active.

Another object of the present invention is to provide a method for separating and purifying the abovementioned polysaccharide P1, which comprises extracting polysaccharides from myrtle fruit by water extraction and alcohol precipitation, and separating and purifying the polysaccharide by ion exchange column chromatography.

A further object of the present invention is to provide a use of the above polysaccharide P1 for preparing a hypolipidemic drug.

The object of the invention is achieved by the following technical solution:

A myrtle polysaccharide P1 comprises the following monosaccharides by molar percentage: 6.74% of ribose, 1.73% of rhamnose, 60.06% of arabinose, 3.54% of xylose, 5.64% of mannose, 13.16% of glucose, and 9.13% of galactose; the content of the monosaccharides are calculated by normalizing the GC-MS areas thereof, wherein the total peak area except the solvent peak is regarded as 100%, and the percentages of each peak area to the total area are calculated.

The myrtle polysaccharide P1 has a number average molecular weight of $6.44 \times 10^3$ Da and a weight average molecular weight of $2.04 \times 10^4$ Da.

A method for separating and purifying the myrtle polysaccharide P1 comprises the following steps:

(1) extraction of a crude myrtle fruit polysaccharide: drying and pulverizing the myrtle fruit, filling the obtained dry powder and distilled water to a reflux device to boil for extraction for several times; then combining the extracts, concentrating under reduced pressure, adding 95% (V/V) ethanol having a volume of several times of the concentrate to the concentrate, and stirring to let the polysaccharide precipitate uniformly; allowing the mixture to stand at 4° C. for more than 12 hours, collecting the precipitate by centrifugation and drying to obtain the crude myrtle fruit polysaccharide;

wherein said boiling for extraction in step (1) is preferably conducted for 4 h each time; and said centrifugation in step (1) is preferably conducted at a speed of 5000 r/min for 15 min;

(2) decolorizing the crude myrtle fruit polysaccharide by $H_2O_2$ solution: dissolving the crude myrtle fruit polysaccharide and adding distilled water, adjusting the pH to 8.0, and then adding 30% $H_2O_2$ solution with stirring until the color of the solution becomes lighter; and maintaining the temperature at 50° C. for 2 h in a water bath;

wherein the concentration of the crude myrtle fruit polysaccharide dissolved in the distilled water is preferably 0.2 g/mL;

(3) deproteinizing by a Sevag reagent: adding the Sevag reagent to the decolorized polysaccharide solution with a volume ratio of 1:5, shaking and culturing for 20 minutes; standing for 10 minutes followed by centrifugation, removing the lower organic phase and the gel formed by the protein in intermediate layer, chloroform, and n-butanol, and repeating the centrifugation and the removal steps for several times; then, removing the remaining Sevag reagent by rotary evaporation to obtain a deproteinized myrtle fruit polysaccharide solution; collecting precipitate by adding ethanol according to step (1), and drying to obtain a preliminary purified myrtle fruit polysaccharide; wherein said Sevag reagent in step (3) consists of chloroform and n-butanol with a volume ratio of 5:1;

said shaking and culturing in step (3) is preferably conducted at a speed of 150 r/min; and said centrifugation in step (3) is preferably conducted at a speed of 4000 r/min for 10 min;

(4) separation of the myrtle polysaccharide P1 by DEAE-Sepharose fast flow ion exchange column chromatography: packing a column with pretreated DEAE-Sepharose filler, dissolving the preliminary purified myrtle fruit polysaccharide in step (3) in deionized water, filtering with a 0.45 μm microporous membrane, and then applying to the column; eluting by distilled water, collecting the eluate, detecting the absorbance of the eluate at a wavelength of 490 nm by phenol-sulfuric acid method, stopping the collection when the absorbance is near zero, combining the obtained fractions, conducting concentration, dialysis, and lyophilizing to obtain the polysaccharide P1;

wherein said pretreatment of the filler in step (4) comprises the steps of: conducting suction filtration to the filler and rinsing with distilled water; since bubbles are generated during the rinsing process, then deaerating the filler with ultrasonic waves, and standing;

the packing step in step (4) comprises the following steps: slowly adding the filler to the chromatography column (column size: 1.5 cm×20 cm), the bed volume of which is about 20 mL; washing the column with distilled water for 1 h, then washing with 1 mol/L NaCl solution for 1 h, and finally washing with distilled water for 2 h to prepare for loading;

the concentration of the preliminary purified myrtle fruit polysaccharide in step (4) dissolved in deionized water is preferably 50 mg/mL;

the flow rate of the loading and elution in step (4) is preferably 0.5 mL/min;

the dialysis in step (4) comprises transferring the concentrated fraction to a dialysis bag (3000 Da) and dialyzing at 4° C. for 48 hours.

The myrtle polysaccharide P1 has a hypolipidemic effect and is useful in preparation of a hypolipidemic drug;

the drug comprises pharmaceutical acceptable excipients and other active ingredients;

the drug may be one of a tablet, a granule, a capsule, a dropping pill, a sustained release agent, an oral solution, and an injection, etc.

The experimental results of the present invention indicate that the myrtle polysaccharide P1 has a certain ability to bind cholate in vitro. When using cholestyramine (a hypolipidemic drug which achieves a hypolipidemic effect by binding cholate) as a positive control, and treating the binding rate of cholestyramine to various chocolates as 100%, the relative binding rates of myrtle polysaccharide P1 to sodium taurocholate, sodium glycocholate and sodium cholate are 25.28%, 44.56%, and 50.10%, respectively. The results of this experiment showed that the myrtle polysaccharide P1 has a certain hypolipidemic effect.

The invention obtains crude polysaccharide of myrtle fruit by water extraction and alcohol precipitation, decolorization by $H_2O_2$, deproteinizing by a Sevag reagent, and separation and purification by DEAE-Sepharose fast flow ion exchange chromatography column, and has the following advantages as compared with the prior art:

(1) The invention establishes a complete and feasible technical route for extracting, separating, purifying, and studying the structural characteristics and biological activity of myrtle fruit polysaccharides, and provides guidance for the extraction, separation and purification of polysaccharides from wild plant resources.

(2) The water extraction and alcohol precipitation method used in the invention can achieve large scale polysaccharide extraction, which has low cost, good repeatability and high yield, and is suitable for industrial large-scale production.

(3) The DEAE-Sepharose fast flow used in the present invention has better physical and chemical stability and mechanical properties. It also has large exchange capacity, can be cleaned in place, and has little change in bed volume with the change of ionic strength due to different pH value, such that it is suitable for the purification of a large number of crude products due to high flow rate and loading amount.

(4) The invention creatively combines water extraction and alcohol precipitation with separation and purification by ion exchange chromatography for the research of the myrtle fruit polysaccharide and obtains optimal parameters, which provides technical guidance and a new route for extraction and purification of myrtle fruit polysaccharides.

DETAILED DESCRIPTION OF THE EMBODIMENTS

Figure 1:
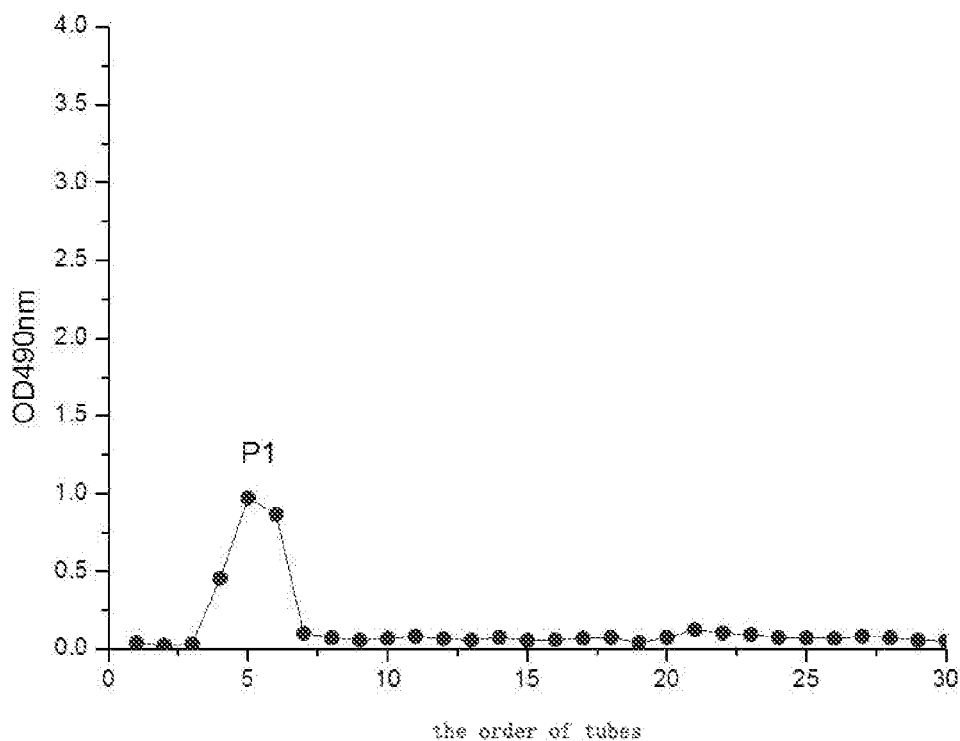
FIG. 1 shows the elution profile of the myrtle fruit polysaccharide.

The present invention will be further described in detail below with reference to the embodiments and drawings, but the embodiments of the present invention are not limited thereto.

In the examples, the analysis of the myrtle fruit polysaccharide P1 was carried out by the Guangzhou Analytical Testing Center, China, and the report number was 2017011500-2.

Example 1

A method for separating and purifying the myrtle polysaccharide P1 comprises the following steps:

(1) extraction of crude myrtle fruit polysaccharide: pulverizing 100 g of dry myrtle fruit, sieving by a 40 mesh sieve and weighing 100 g of the sieved dry powder; adding the obtained dry powder and 1000 mL of distilled water to a reflux device to boil for 4 h; then combining the extracts, concentrating under reduced pressure, adding 95% (V/V) ethanol having a volume of 4 times of the concentrate to the concentrate, and stirring with a glass rod to let the polysaccharide precipitate uniformly; allowing the mixture to stand at 4° C. for 12 hours, collecting the precipitate by centrifugation at a speed of 5000 r/min for 15 min and drying to obtain the crude myrtle fruit polysaccharide;

(2) decolorizing the crude myrtle fruit polysaccharide by $H_2O_2$ solution: dissolving the crude myrtle fruit polysaccharide in 100 mL of distilled water, adjusting the pH to 8.0 by 1% NaOH solution, and then adding 30% $H_2O_2$ solution with stirring until the color of the solution becomes lighter; and maintaining the temperature at 50° C. for 2 h in a water bath;

(3) deproteinizing by a Sevag reagent: adding the Sevag reagent consisting of chloroform and n-butanol with a volume ratio of 5:1 to the decolorized polysaccharide solution with a volume ratio of 1:5, shaking at a speed of 150 r/min in a shaker for 20 minutes; standing for 10 minutes followed by centrifugation, removing the lower organic phase and the gel formed by the protein in intermediate layer, chloroform, and n-butanol, and repeating the centrifugation and the removal steps for 5 times; then, removing the remaining Sevag reagent by rotary evaporation after centrifuging for the last time at a speed of 4000 r/min for 10 min to obtain a deproteinized myrtle fruit polysaccharide solution; collecting precipitate by adding ethanol according to step (1), and drying to obtain a preliminary purified myrtle fruit polysaccharide;

(4) separation of the myrtle polysaccharide P1 by DEAE-Sepharose fast flow ion exchange column chromatography:

4.1 pretreatment of the filler: in order to remove a 20% ethanol protection solution, rinsing with distilled water during suction filtration; and since bubbles are generated during the rinsing process, removing the bubbles by ultrasonic wave and allowing to stand;

4.2 packing: slowly adding the filler to a column (column size is 1.5 cm×20 cm), the bed volume of which is about 20 mL; washing the column with distilled water for 1 h, then washing with 1 mol/L NaCl solution for 1 h, and finally washing with distilled water for 2 h to prepare for loading;

4.3 loading: dissolving 0.1 g of polysaccharide sample in 2 mL of distilled water and preparing a 50 mg/mL solution; after filtering with a 0.45 μm microporous membrane, loading the sample at 0.5 mL/min;

4.4 elution: eluting with distilled water at a flow rate of 0.5 mL/min, collecting one tube of eluate per 5 mL, determining the polysaccharide content of each tube by phenol-sulfuric acid method, and stopping the collection until no polysaccharide is detected. Plotting the absorbance at a wavelength of 490 nm against the order of tubes, such that an elution curve is obtained and shown in FIG. 1;

The specific operation of the phenol-sulfuric acid method for detecting the polysaccharide content is as follows: accurately filling 0, 0.2, 0.4, 0.6, 0.8, and 1.0 mL of 0.1 mg/mL anhydrous glucose standard solution in 6 test tubes, then adding 1.0, 0.8, 0.6, 0.4, 0.2, and 0 mL of distilled water in order, and adding 0.5 mL of 6% phenol solution and 2.5 mL of concentrated sulfuric acid successively. After mixing, standing for 20 min at room temperature, and measuring the absorbance at a wavelength of 490 nm. The absorbance is plotted against the concentration of glucose to obtain a standard curve. The absorbance of 1 mL of each tube of the sample solution is measured under the same condition as that of the standard curve to calculate the total polysaccharide content in each tube of the sample solution.

4.5 dialysis: collecting the eluted fractions separately, transferring the concentrated fractions to a dialysis bag (3000 Da) and dialyzing at 4° C. for 48 hours, concentrating them under reduced pressure, and lyophilizing to obtain the myrtle fruit polysaccharide P1.

Example 2

The myrtle fruit polysaccharide P1 obtained in Example 1 was subjected to UV analysis. 1 mg of the polysaccharide sample was weighed to prepare a 1 mg/ml polysaccharide solution, and the ultraviolet spectrum was scanned in the range of 200-500 nm.

Figure 2:
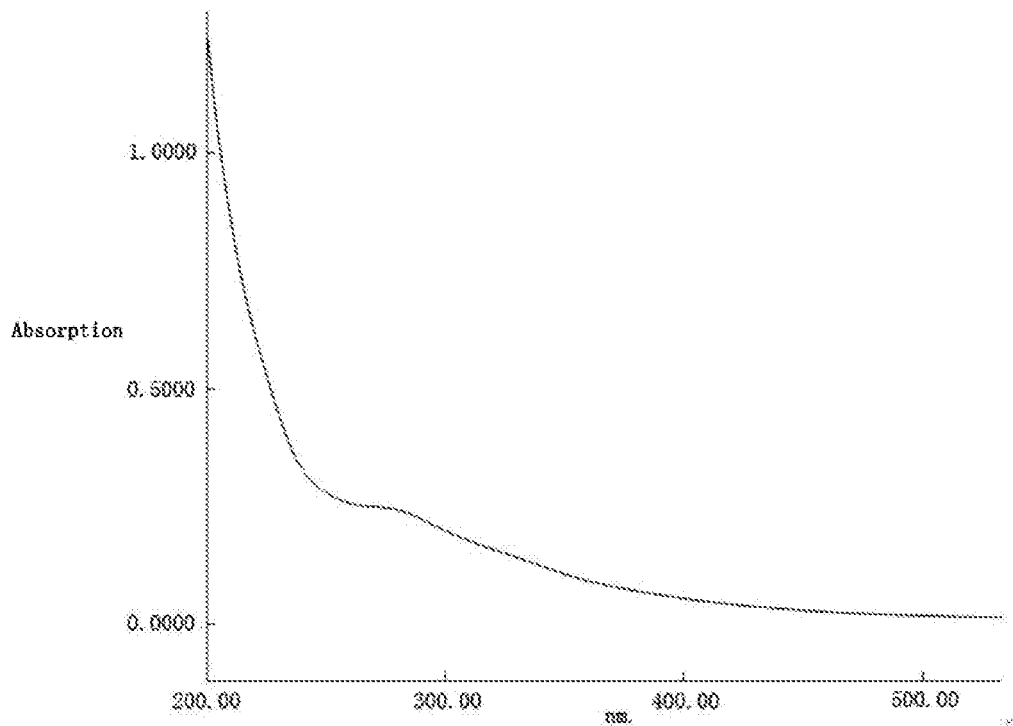
FIG. 2 is a UV spectrum of polysaccharide P1.

FIG. 2 is an ultraviolet spectrum of P1. It shows that the product has no obvious absorption peak at 260 nm and at 280 nm, indicating that it does not contain protein and nucleic acid substances.

Example 3

The molecular weight of myrtle fruit polysaccharide P1 obtained in Example 1 was analyzed by the following method.

The molecular weight was determined by gel permeation chromatography (GPC). 2 mg of polysaccharide sample was dissolved in a 0.02 mol/L phosphate buffer solution to prepare a 2.0 mg/mL solution. Then the solution was filtered with a 0.22 μm sterile filter membrane, and the filtered solution was stored for use. Chromatographic conditions were as follows: column temperature was 35° C., 0.02 mol/L phosphate buffer was used as mobile phase, flow rate was at 0.6 mL/min, injection volume was 20 μL, and Waters 2410 differential refractive index detector was used. A series of dextran solutions with different molecular weight (700, 400, 200, 100, 50, 30, 10, 5 kD) were used as standard to draw a standard curve, and the molecular weight of the sample was calculated with the standard curve according to its corresponding elution volume.

The molecular weight of the purified myrtle fruit polysaccharide was measured as shown in Table 1 below:

TABLE 1

The molecular weight of the myrtle fruit polysaccharide

| component | Mn (Da) | Mw (Da) | Mw/Mn |
|---|---|---|---|
| P1 | $6.44 \times 10^3$ | $2.04 \times 10^4$ | 3.17 |

Example 4

The monosaccharide composition of the myrtle fruit polysaccharide P1 obtained in Example 1 was analyzed by the following method.

5 mL of 4 mol/L trifluoroacetic acid was added to 10 mg of the polysaccharide sample, and the mixture was hydrolyzed at 100° C. for 2 hours. The hydrolyzate was dried by a nitrogen gas blower and washed three times with chromatographically pure methanol to obtain a polysaccharide hydrolyzate. 10 mg of hydroxylamine hydrochloride, 1 mg of internal standard inositol and 2 mL of pyridine were sequentially added to the polysaccharide hydrolyzate. After 90 min of water bath at 90° C., 2 mL of acetic anhydride was added. After 90 min of water bath at 90° C., 2 mL of distilled water was added to terminate the reaction. The resulted mixture was extracted twice with 2 mL of dichloromethane, and the dichloromethane phase was combined, dried over anhydrous sodium sulfate, and filtered by a 0.22 μm organic microporous membrane.

Gas chromatographic conditions: analytical column was HP-5MS (30 m×0.25 mm×0.25 μm); injection volume was 1 μL; inlet temperature was 250° C.; constant pressure was 20 PSI; programmed temperature: column temperature was kept at 100° C. for 0.5 min, raised to 140° C. at a speed of 20° C./min for 5 min, increased to 160° C. at a speed of 3° C./min, and then increased to 250° C. at a speed of 10° C./min for 5 min; split ratio was set as 10:1, the mobile phase was helium and the flow rate was 1 mL/min.

Monosaccharide standard test: ribose, rhamnose, arabinose, xylose, mannose, glucose, galactose standard were tested according to the same method as above as standard controls.

The measured monosaccharide composition of the myrtle fruit polysaccharide is shown in Table 2 below:

TABLE 2

The monosaccharide composition of the myrtle fruit polysaccharide

| component | Molar ratio (%) | | | | | | |
|---|---|---|---|---|---|---|---|
| | Rib | Rha | Ara | Xyl | Man | Glu | Gal |
| P1 | 6.74 | 1.73 | 60.06 | 3.54 | 5.64 | 13.16 | 9.13 |

Example 5

Fourier infrared spectroscopy analysis of the myrtle fruit polysaccharide P1 obtained in Example 1 was carried out.

2 mg of the polysaccharide sample was mixed with dried KBr in a mortar. The mixture was pressed into a tablet by a tableting machine, and a Fourier transform infrared spectrometer was used to scan a spectrum with wave number at 400-4000 cm$^{-1}$.

Figure 4:
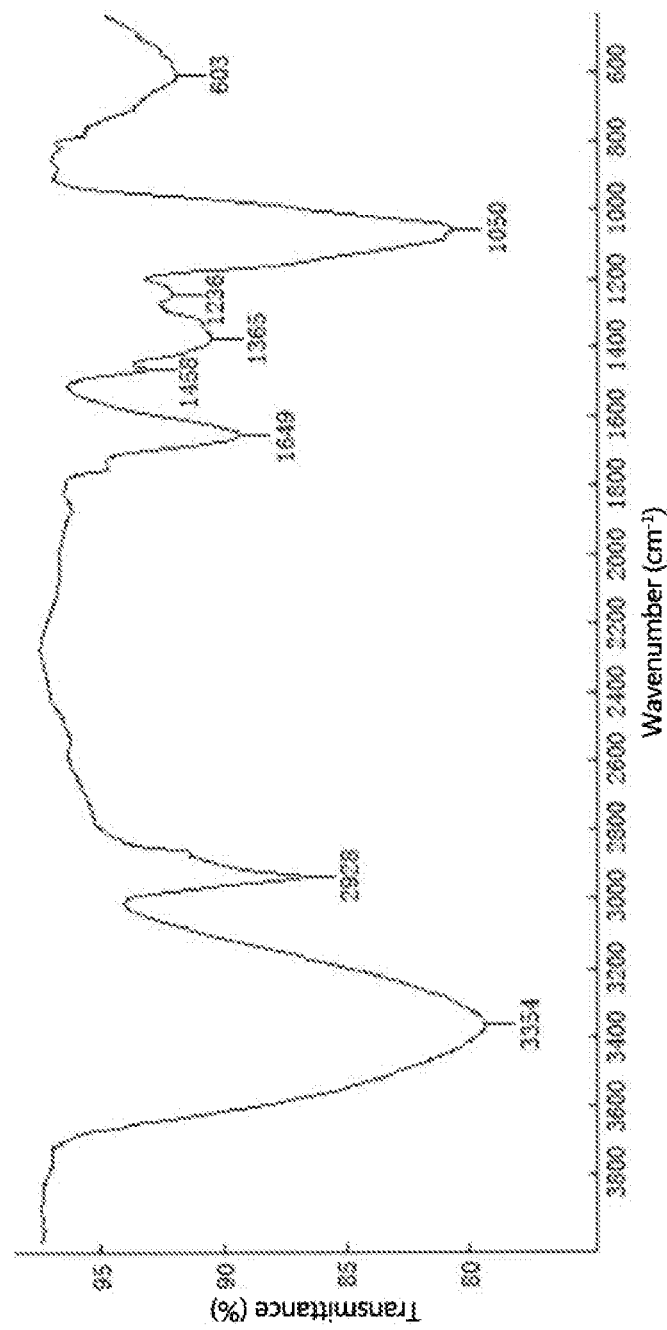
FIG. 4 is an infrared spectrum of polysaccharide P1.

Functional groups have characteristic absorption peaks in infrared spectrum, and therefore, infrared spectrum can better analyze the structure of the polysaccharide. FIG. 4 is an infrared spectrum of the purified myrtle fruit polysaccharide P1, the absorption peak at 3354 cm$^{-1}$ is resulted from OH stretching vibration, and the absorption peak at 2928 cm$^{-1}$ is resulted from CH stretching vibration, and the absorption peak at 1458 cm$^{-1}$ is resulted from CO stretching vibration. These peaks are characteristic peaks of polysaccharide, and it can be deduced that P1 should be a polysaccharide.

In the infrared spectrum of P1 (FIG. 4), there is a distinct absorption peak at 1649 cm$^{-1}$, which is a characteristic absorption peak of bound water; the absorption peak at 1236 cm$^{-1}$ is resulted from the stretching vibration of S=O, indicating sulfate group is present in P1; the absorption peak at 1050 cm$^{-1}$ illustrates the presence of glucose units.

Example 6

The in vitro cholate binding capacity of the myrtle fruit polysaccharide P1 obtained in Example 1 was tested, and cholestyramine was used as a positive control to preliminarily characterize the hypolipidemic ability of the polysacchride. The method is as follows.

Preparation of standard curve of cholate: 0.3 mmol/L sodium taurocholate, sodium glycocholate, and sodium cholate solution were prepared with 0.1 mol/L and pH=6.3 phosphate buffer solution, respectively. 0, 0.1, 0.5, 1.0, 1.5, 2.0, and 2.5 mL of the above solutions were added respectively in a 10 mL stoppered test tube. 0.1 mol/L, pH=6.3 phosphate buffer solution was further added to the test tubes until the volume became 2.5 mL. Then 7.5 mL of 60 wt % sulfuric acid solution was added and the temperature was kept at 70° C. in a water bath for 20 min. After that the test tubes were taken out and placed in an ice bath for 5 min, and absorbance at 387 nm wavelength was detected respectively. The absorbance was plotted against the concentration of cholate to prepare a standard curve.

Simulation of the human gastrointestinal environment: 1 mL of the sample solution and 1 mL of 0.01 mol/L hydrochloric acid solution were added to a 10 mL stoppered test tube, and the mixture was shaken and digested at 37° C. for 1 h. Then pH was adjusted with a 0.1 mol/L sodium hydroxide solution to 6.3, followed by the addition of 4 mL of 10 mg/mL trypsin (prepared with 0.1 mol/L phosphate buffer at pH 6.3). The mixture was further shaken and digested at 37° C. for 30 min.

In vitro binding of cholate: 4 mL of 0.3 mmol/L cholate solutions (sodium taurocholate, sodium glycocholate, sodium cholate) were added to the simulated human gastrointestinal environment respectively. The solutions were shaken at 37° C. for 1 h, then transferred to a centrifuge tube and centrifuged at 4000 r/min for 20 min. The content of cholate in the obtained supernatants were analyzed: 2.5 ml of each of the supernatants and 7.5 ml of 60% sulfuric acid solution were added sequentially to a stoppered test tube. The test tubes were kept in a water bath at 70° C. for 20 min, and then in an ice bath for 5 min. The absorbance was measured at 387 nm. The concentration of cholate in the sample solution was determined from the standard curve, which may be subtracted from the concentration of the added cholate to calculate the concentration of bound cholate.

Figure 3:
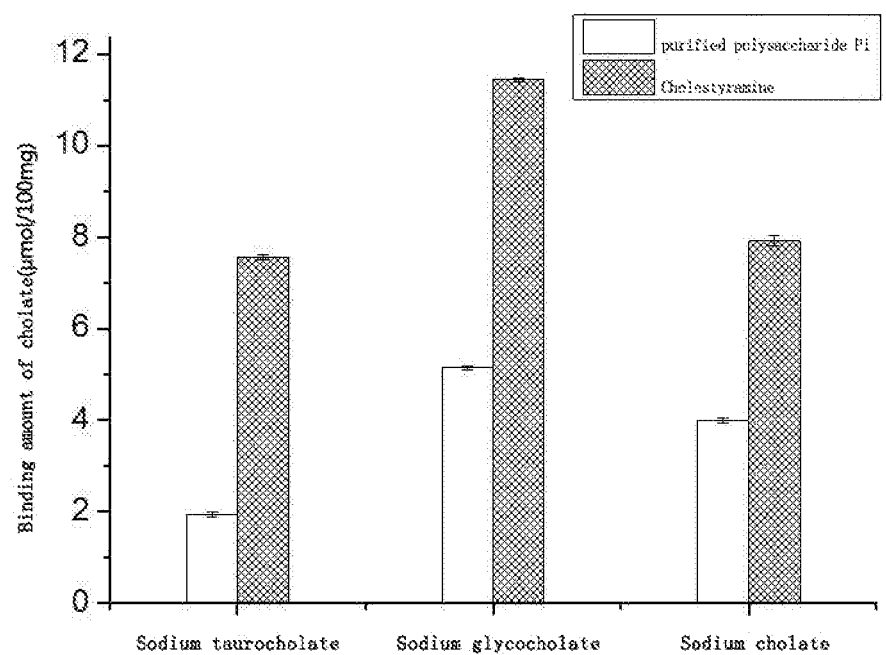
FIG. 3 shows the ability of myrtle fruit polysaccharide to bind cholate in vitro.

FIG. 3 shows the ability of the purified myrtle fruit polysaccharide P1 to bind cholate in vitro. The result shows that cholestyramine (a hypolipidemic drug which achieves a hypolipidemic effect by combination with cholate) was used as a positive control. Taking the binding rate of cholestyramine to each cholate as 100%, the relative binding rate of the myrtle polysaccharide P1 to sodium taurocholate, sodium glycocholate and sodium cholate was 25.28%, 44.56%, and 50.10%, respectively.

The above embodiments are preferred embodiments of the present invention, but the embodiments of the present invention are not limited to the above embodiments, and any other changes, modifications, substitutions, combinations, and simplifications thereof made without departing from the spirit and scope of the invention should all be equivalent replacements and be included in the scope of the present invention.

The invention claimed is:

1. A method for separating and purifying myrtle polysaccharide P1, comprising the following steps:
    (1) drying and pulverizing the myrtle fruit, filing the obtained dry powder and distilled water to a reflux device to boil for extraction for several times; then combining the extracts, concentrating under reduced pressure, adding 95% (V/V) ethanol having a volume of several times of the concentrate to the concentrate, and stirring to let the polysaccharide precipitate uniformly; allowing the mixture to stand at 4° C. for more than 12 hours, collecting the precipitate by centrifugation and drying to obtain the crude myrtle fruit polysaccharide;
    (2) decolorizing the crude myrtle fruit polysaccharide by adding 30% $H_2O_2$ solution;
    (3) adding the decolorized polysaccharide to a Sevag reagent for deproteinizing to obtain a preliminary purified myrtle fruit polysaccharide;
    (4) packing a column with pretreated DEAE-Sepharose filler, dissolving the preliminary purified myrtle fruit polysaccharide in step (3) in deionized water, filtering with a 0.45 μm microporous membrane, and then applying to the column; eluting by distilled water, collecting the eluate, detecting the absorbance of the eluate at a wavelength of 490 nm by phenol-sulfuric acid method, stopping the collection when the absorbance is near zero, combining the obtained fractions, conducting concentration, dialysis, and lyophilizing to obtain the polysaccharide P1; wherein the polysaccharide P1 comprises the following monosaccharides by molar percentage: 6.74% of ribose, 1.73% of rhamnose, 60.06% of arabinose, 3.54% of xylose, 5.64% of mannose, 13.16% of glucose, and 9.13% of galactose; wherein the polysaccharide P1 has a number average molecular weight of $6.44 \times 10^3$ Da and a weight average molecular weight of $2.04 \times 10^4$ Da; and wherein the polysaccharide P1 has an ability to bind cholate in vitro and has a hypolipidemic effect, and when treating a binding rate of cholestyramine to each choate as 100%, a relative binding rate of the polysaccharide P1 to sodium taurocholate, sodium glycocholate and sodium cholate is 25.28%, 44.56%, and 50.10%, respectively.

2. The separation and purification method according to claim 1, wherein step (2) comprises the following steps: dissolving the crude myrtle fruit polysaccharide and adding distilled water, adjusting the pH to 8.0, and then adding 30% $H_2O_2$ solution with stirring until the color of the solution becomes lighter; and maintaining the temperature at 50° C. for 2 h in a water bath.

3. The separation and purification method according to claim 1, wherein step (3) comprises the following steps: adding the Sevag reagent to the decolorized polysaccharide solution with a volume ratio of 1:5, shaking and culturing for 20 minutes; standing for 10 minutes followed by centrifugation, removing the lower organic phase and the gel formed by the protein in intermediate layer, chloroform, and n-butanol, and repeating the centrifugation and the removal steps for several times; then, removing the remaining Sevag reagent by rotary evaporation to obtain a deproteinized myrtle fruit polysaccharide solution; collecting precipitate by adding ethanol according to step (1), and drying to obtain a preliminary purified myrtle fruit polysaccharide.

4. The separation and purification method according to claim 1, wherein the flow rate of the loading and elution in step (4) is 0.5 mL/min.

* * * * *

UNITED STATES PATENT AND TRADEMARK OFFICE
CERTIFICATE OF CORRECTION

PATENT NO. : 11,369,627 B2
APPLICATION NO. : 16/435677
DATED : June 28, 2022
INVENTOR(S) : Ruqiang Huang et al.

It is certified that error appears in the above-identified patent and that said Letters Patent is hereby corrected as shown below:

In the Claims

Column 8, Line 16, Claim 1, insert --a-- after "separating and purifying"

Signed and Sealed this
Eighteenth Day of October, 2022

Katherine Kelly Vidal
*Director of the United States Patent and Trademark Office*